(12) United States Patent
Rocci et al.

(10) Patent No.: US 12,408,931 B2
(45) Date of Patent: Sep. 9, 2025

(54) SURGICAL INSTRUMENT HAVING A SELF-CENTERED QUICK CONNECT INTERFACE

(71) Applicant: DePuy Synthes Products, Inc., Raynham, MA (US)

(72) Inventors: Mirko Rocci, Oberdorf (CH); Martin Altmann, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 31 days.

(21) Appl. No.: 18/545,720

(22) Filed: Dec. 19, 2023

(65) Prior Publication Data
US 2025/0195084 A1    Jun. 19, 2025

(51) Int. Cl.
*A61B 17/16*    (2006.01)

(52) U.S. Cl.
CPC ........ *A61B 17/162* (2013.01); *A61B 17/1617* (2013.01)

(58) Field of Classification Search
CPC . A61B 17/16; A61B 17/1613; A61B 17/1615; A61B 17/1617; A61B 17/162; A61B 17/1622; A61B 17/1624; A61B 17/1626; A61B 17/1628; A61B 17/1633; A61B 17/1655; A61B 17/1657; B25B 23/0035; B25G 3/12; B25G 3/18; B25G 3/20; B25G 3/22; B25G 3/26
See application file for complete search history.

(56) References Cited

U.S. PATENT DOCUMENTS

| | | | |
|---|---|---|---|
| 6,270,085 B1 * | 8/2001 | Chen | B25B 21/007 279/22 |
| 7,448,302 B2 * | 11/2008 | Huang | B25B 23/0035 81/177.85 |
| 7,740,249 B1 * | 6/2010 | Gao | B23B 31/1071 279/22 |

(Continued)

FOREIGN PATENT DOCUMENTS

CA    2725713 C    8/2002

OTHER PUBLICATIONS

International Search Report and Written Opinion; PCT/IB2024/062395; May 6, 2025; 8 pgs.

*Primary Examiner* — Eric S Gibson
(74) *Attorney, Agent, or Firm* — Dunlap Codding, P.C.

(57) ABSTRACT

A quick connect tool, a replaceable tool, and methods are disclosed. The replaceable tool includes a shaft having a tool end, a coupling end opposite the tool end, and a longitudinal axis extending between the coupling end and the tool end. The shaft has a tool portion defining the tool end, a coupling portion defining the coupling end, the coupling portion having an outer peripheral surface shaped into a flat portion coextensive with an arcuate portion cooperatively forming a D-shaped cross-section. The flat portion and the arcuate portion extend along the longitudinal axis. The outer peripheral surface defines a peripheral groove extending transversely with respect to the longitudinal axis. The peripheral groove is configured to receive a bearing, and the outer peripheral surface also defines a bearing surface having a shape conforming to a partial spiral extending around the longitudinal axis and located at the coupling end of the shaft.

23 Claims, 8 Drawing Sheets

(56) References Cited

U.S. PATENT DOCUMENTS

| | | | | |
|---|---|---|---|---|
| 7,810,817 B1* | 10/2010 | Gao | ............... | A61B 17/162 |
| | | | | 279/75 |
| 7,922,180 B2* | 4/2011 | Meng | ............... | B25B 15/001 |
| | | | | 279/143 |
| 8,985,593 B1* | 3/2015 | Gao | ............... | B25G 3/12 |
| | | | | 279/74 |
| 9,447,803 B1* | 9/2016 | Fu | ............... | A61B 17/8875 |
| 9,458,890 B1* | 10/2016 | Fu | ............... | F16D 1/108 |
| 10,849,634 B2* | 12/2020 | Nguyen | ............... | A61B 17/1622 |
| 10,905,453 B2* | 2/2021 | Cihak | ............... | B23B 31/1071 |
| 10,993,728 B2* | 5/2021 | Reed | ............... | A61B 17/1615 |
| 11,154,319 B2* | 10/2021 | Dexter | ............... | A61B 17/3205 |
| 11,540,840 B2* | 1/2023 | Cannon | ............... | A61B 17/162 |
| 12,082,825 B2* | 9/2024 | Hilton | ............... | B23B 31/20 |
| 12,137,918 B2* | 11/2024 | Nguyen | ............... | A61B 17/1624 |
| 2005/0036844 A1* | 2/2005 | Hirt | ............... | B25B 23/0035 |
| | | | | 408/240 |
| 2010/0286694 A1 | 11/2010 | Rio et al. | | |
| 2016/0278802 A1* | 9/2016 | Cihak | ............... | A61B 17/162 |
| 2019/0201009 A1* | 7/2019 | Reed | ............... | A61B 17/1615 |
| 2019/0388115 A1* | 12/2019 | Nguyen | ............... | A61B 17/162 |
| 2022/0192681 A1* | 6/2022 | Hilton | ............... | B23B 31/008 |

* cited by examiner

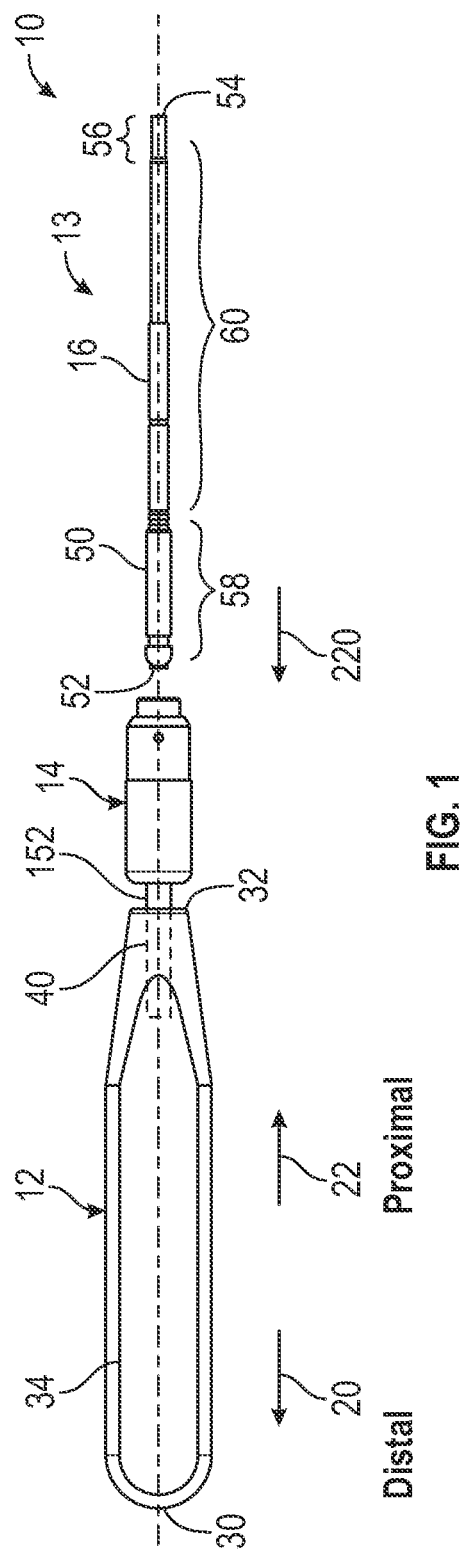
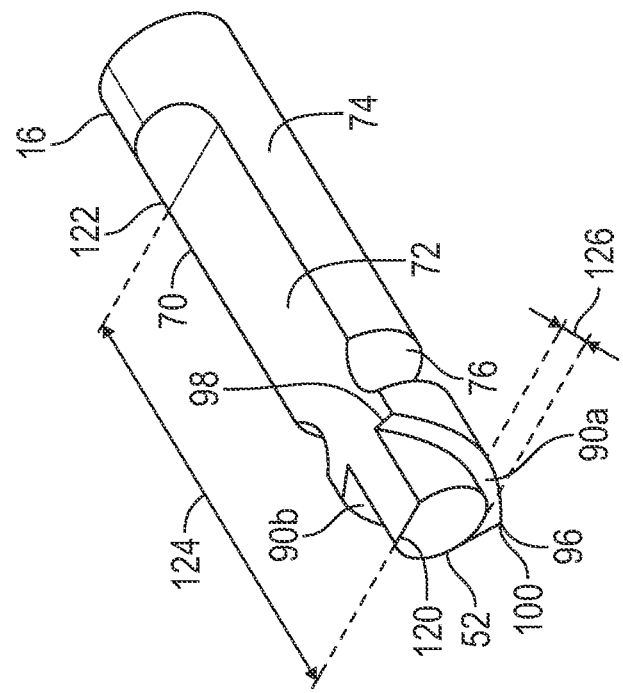
FIG. 1
FIG. 2A

SURGICAL INSTRUMENT HAVING A SELF-CENTERED QUICK CONNECT INTERFACE

CROSS-REFERENCE TO RELATED APPLICATIONS

Not Applicable.

STATEMENT AS TO RIGHTS TO INVENTIONS MADE UNDER FEDERALLY SPONSORED RESEARCH AND DEVELOPMENT

Not applicable.

BACKGROUND ART

Quick connect interfaces (or simply "quick connects") are widely used in surgical instruments to connect a replaceable tool, such as a bit, to a drive mechanism, a ratcheting or non-ratcheting handle, or a motor-operated drive. These surgical instruments may be used to perform a variety of surgical tasks, including drilling, reaming, tapping, placement of bone screws, assembly of spinal constructs, and the like. One common type of quick connect interface that may be employed is an Association for Osteosynthesis (AO)-style quick connect interface, typically referred to simply as an "AO quick connect interface." Such an interface may be used with a wide variety of different types of replaceable tools, as well as different drive mechanisms.

A typical AO quick connect interface includes a body member configured to receive a coupling end of a shaft having a D-shaped profile. The D-shaped profile defines a flat portion configured to extend past and engage another flat portion (referred to herein as the "AO flat") formed in an inner cavity of the body member of the AO quick connect interface. This engagement prevents the rotation of the shaft with respect to the body member. The conventional AO quick connect interface also includes one or two openings in the body member, and one or two ball bearings. Each ball bearing is positioned within one of the one or two openings, and a sleeve surrounds the body member. The shaft may be retained in the body member by the operation of the ball bearing. The opening extends from an exterior of the body member to the inner cavity within the body member. The ball bearing can be positioned partially within the inner cavity and engage a groove formed in the end of the shaft of the replaceable tool. The ball bearing is held in this engaged position by a substantially straight-walled portion of an interior of the sleeve.

One of the challenges of the conventional AO coupling is for a user to align the flat portion on the coupling end of the replaceable tool with the flat portion forming a boundary of the inner cavity within the body member. The conventional AO Coupling requires the user to partially insert the coupling end of the replaceable tool into the inner cavity, and then rotate the replaceable tool relative to the body member of the quick connect coupling while forcing the replaceable tool into the inner cavity until the flat portion of the replaceable tool is aligned with the flat portion in the inner cavity. Once the flat portion of the replaceable tool is aligned with the flat portion of the inner cavity, the user can move the coupling end of the replaceable tool further into the inner cavity, thereby seating the coupling end of the replaceable tool into the inner cavity. The replaceable tool and the conventional AO coupling lack any mechanism constructed to guide the flat portions of the replaceable tool and the inner cavity into alignment. This causes surgeons and their assistants to fiddle with the replaceable tool and the AO coupling attached to the selected drive mechanism in the middle of surgery, in order to seat the coupling end of the replaceable tool into the inner cavity.

SUMMARY OF THE INVENTION

To this end, a need exists for an improved coupling assembly, conforming to standards set by the Association for Osteosynthesis, that includes a replaceable tool and a quick connect interface constructed to guide the flat areas on the replaceable tool and within the inner cavity into alignment, to more easily seat the coupling end of the replaceable tool into a bore of a body member of the quick connect interface. It is to such an improved coupling assembly that the inventive concepts disclosed herein are directed. In one aspect, the problem of seating the replaceable tool into the quick connect interface is addressed by forming a bearing surface on a coupling end of the replaceable tool and an alignment surface on an alignment member within a bore of the quick connect interface such that that when a coupling end of the replaceable tool is positioned within the bore, the bearing surface of the replaceable tool engages the alignment surface and causes rotary motion of the replaceable tool so as to align the coupling end of the replaceable tool with the bore.

In some embodiments, the bearing surface has a partial spiral shape and is positioned on a coupling portion having a D-shaped cross-section of a shaft of the replaceable tool. The shaft has a tool end opposite to a coupling end, and a longitudinal axis extending from the tool end to the coupling end. The coupling portion extends from the coupling end towards the tool end.

BRIEF DESCRIPTION OF THE DRAWINGS

The accompanying drawings, which are incorporated in and constitute a part of this specification, illustrate one or more implementations described herein and, together with the description, explain these implementations. The drawings are not intended to be drawn to scale, and certain features and certain views of the figures may be shown exaggerated, to scale or in schematic in the interest of clarity and conciseness. Not every component may be labeled in every drawing. Like reference numerals in the figures may represent and refer to the same or similar element or function. In the drawings:

FIG. 1 is a side elevational view of a surgical instrument that includes a coupling assembly having a replaceable tool and a quick connect interface constructed in accordance with the present disclosure attached to a drive mechanism.

FIG. 2A is a perspective view of a coupling portion of a shaft of the replaceable tool of FIG. 1.

DETAILED DESCRIPTION

Figure 2B:
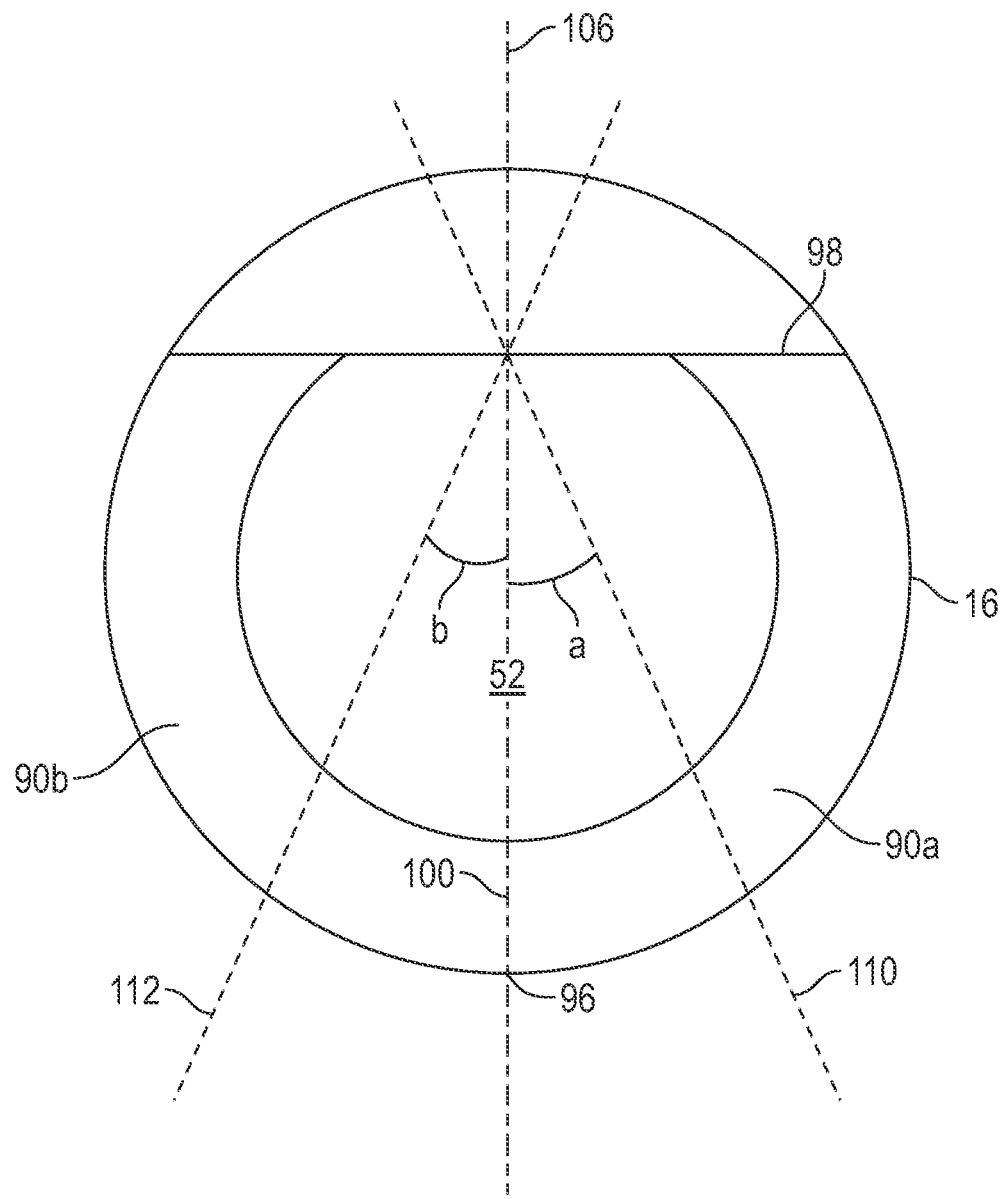
FIG. 2B is an end view of the coupling portion of the shaft of the replaceable tool of FIG. 1.

The following detailed description refers to the accompanying drawings. The same reference numbers in different drawings may identify the same or similar elements.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or more and the singular also includes the plural unless it is obvious that it is meant otherwise.

Further, use of the term "plurality" is meant to convey "more than one" unless expressly stated to the contrary.

As used herein, qualifiers like "substantially," "about," "approximately," and combinations and variations thereof, are intended to include not only the exact amount or value that they qualify, but also some slight deviations therefrom, which may be due to manufacturing tolerances, measurement error, wear and tear, stresses exerted on various parts, and combinations thereof, for example.

The use of the term "at least one" or "one or more" will be understood to include one as well as any quantity more than one. In addition, the use of the phrase "at least one of X, V, and Z" will be understood to include X alone, V alone, and Z alone, as well as any combination of X, V, and Z.

The use of ordinal number terminology (i.e., "first", "second", "third", "fourth", etc.) is solely for the purpose of differentiating between two or more items and, unless explicitly stated otherwise, is not meant to imply any sequence or order or importance to one item over another or any order of addition.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50. Similarly, fractional amounts between any two consecutive integers are intended to be included herein, such as, but not limited to, 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, and 0.95. For example, the range 3 to 4 includes, but is not limited to, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, and 3.95. Thus, even if specific data points within the range, or even no data points within the range, are explicitly identified or specifically referred to, it is to be understood that any data points within the range are to be considered to have been specified, and that the inventor possessed knowledge of the entire range and the points within the range.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Referring now to the figures, and in particular to FIG. 1, shown therein is a surgical instrument 10 including a drive mechanism 12 attached to a coupling assembly 13. The coupling assembly 13 includes a quick connect interface 14, and a replaceable tool 16. The quick connect interface 14 As will be described in more detail below, the quick connect interface 14 and the replaceable tool 16 of the surgical instrument 10 are configured to provide a self-centering function when the replaceable tool 16 is placed within the quick connect interface 14. Other than the components providing the self-centering function described below, the quick connect interface 14 may be constructed to conform to the requirements of an Association for Osteosynthesis (AO)-style quick connect interface, typically referred to simply as an "AO quick connect interface.

The components of the surgical instrument 10 will now be described in detail. As shown in FIG. 1, the drive mechanism 12 is coupled to the quick connect interface 14. In this example, the drive mechanism 12 is a non-ratcheting molded handle. Alternatively, the drive mechanism 12 may be implemented in other ways. For example, the drive mechanism 12 may include ratcheting and non-ratcheting handles or a motor-operated drive (such as a battery-powered drive). The surgical instrument 10 may include a longitudinal axis 18 extending through a center of the drive mechanism 12, the quick connect interface 14, and the replaceable tool 16 of the surgical instrument 10. The longitudinal axis 18 may extend in both a first direction 20, and a second direction 22. The replaceable tool 16 (in this example, a star drive bit) is configured to be removably coupled to the quick connect interface 14 to permit replacement of the replaceable tool 16.

The drive mechanism 12, as shown in FIG. 1, is provided with a first end 30, a second end 32, and a handle portion 34 extending between the first end 30 and the second end 32. In the example shown, the handle portion 34 is configured to be gripped by an individual. In this regard, the handle portion 34 may be provided with a substantially cylindrical shaped cross-section, hex-shaped cross-section, or octagonal shaped cross-section to facilitate the handle portion 34 being securely gripped by the individual. To receive and securely receive the quick connect interface 14, the handle portion 34 may be provided with a bore 40 extending through the second end 32 towards the first end 30. The bore 40 may be aligned with the longitudinal axis 18 as shown in FIG. 1. It should be understood that the bore 40 may extend sufficiently into the handle portion 34 so as to securely receive a portion of the quick connect interface 14 therein. It should also be understood that the bore 40 may be shaped so as to receive the portion of the quick connect interface 14 without permitting rotation of the portion relative to the handle portion 34. For example, the bore 40 may be provided with a square shaped cross-section, or a hex shaped cross-section for example.

The replaceable tool 16, as shown in FIG. 1, is provided with a shaft 50 having a tool end 52, and a coupling end 54. The shaft 50 is provided with a tool portion 56, a coupling portion 58, and an intermediate portion 60 extending between the tool portion 56 and the coupling portion 58. The tool portion 56, the coupling portion 58, and the intermediate portion 60 can all be integrally formed as a single unit. In other embodiments, the tool portion 56, the coupling portion 58, and the intermediate portion 60 can be separate elements that are connected together.

As shown in FIG. 1, the tool portion 56 is located at the tool end 54 of the shaft 50. Similarly, the coupling portion 58 is located at the coupling end 52 of the shaft 50. The tool portion 56, the coupling portion 58 and the intermediate portion 60 may all extend on the longitudinal axis 18. Also, the coupling end 52 may be opposite to the tool end 56.

Referring to FIG. 1 in combination with FIG. 2A, the coupling portion 58 is provided with an outer peripheral surface 70 shaped into a flat portion 72 coextensive with an arcuate portion 74 cooperatively forming a D-shaped cross-section. The flat portion 72 and the arcuate portion 74 extend along at least a portion of the longitudinal axis 18 from the tool end 52 towards the intermediate portion 60. The outer peripheral surface 70 also defines a peripheral groove 76 extending transversely with respect to the longitudinal axis 18.

As will be discussed in more detail below, the quick connect interface 14 is provided with a bearing 80 (see FIG. 3A). The bearing 80 may be a ball bearing, for example. The peripheral groove 76 in some embodiments is configured to receive at least a portion of the bearing 80 to maintain the coupling portion 58 within the quick connect interface 14. The bearing 80 may conform to the requirements of the Association for Osteosynthesis-style quick connect interface. Likewise, the flat portion 72, the arcuate portion 74, and the peripheral groove 76 may also conform to the requirements of the Association for Osteosynthesis style quick connect interface.

The outer peripheral surface 70 of the coupling portion 58 also defines at least one, and preferably two bearing surface (s) 90 with each bearing surface 90 having a shape conforming to a partial spiral extending around the longitudinal axis 18 and located at the coupling end 52 of the shaft 50.

In the example shown, the at least one bearing surface 90 includes a first bearing surface 90a and a second bearing surface 90b. The first bearing surface 90a extends from the coupling end 52 in a counterclockwise direction around the longitudinal axis 18 and towards the intermediate portion 60. And, the second bearing surface 90b extends in a clockwise direction around the longitudinal axis 18 and towards the intermediate portion 60. Otherwise, the first bearing surface 90a and the second bearing surface 90b are identical in construction and function. For purposes of brevity, the first bearing surface 90a will be described in detail hereinafter. And such description, is equally applicable to the second bearing surface 90b.

The first bearing surface 90a has a first end 96 and a second end 98 opposed from the first end 96. In the example shown, the first end 96 originates at the coupling end 52 of the shaft 50 and the second end 98 terminates at the flat portion 72 of the outer peripheral surface 70 of the shaft 50. In some embodiments, should be understood that the first end 96 may originate a distance from the coupling end 52 of the shaft 50. The first bearing surface 90a extends at an angle between 30° and 150° relative to the longitudinal axis 18 of the shaft 50 of the replaceable tool 16.

As best shown in FIGS. 2A and 2B, the first bearing surface 90a and the second bearing surface 90b meet at a meeting location 100, which may form an apex at the intersection of the first bearing surface 90a and the second bearing surface 90b. The first bearing surface 90a and the second bearing surface 90b may meet within a distance of 0 mm to 2 mm from the coupling end 52 of the shaft 50.

As best shown in FIG. 2B, the meeting location 100 may be linear and extend along a transverse axis 106. The transverse axis 106 may be normal to the flat portion 72. In some embodiments, the meeting location 100 may be offset radially from the transverse axis 106. For example, a first axis 110 and a second axis 112 may intersect the transverse axis 106. The first axis 110 may be radially offset an angle a within a range of about 0 degrees to about 30 degrees from the transverse axis 106. The second axis 112 may be radially offset an angle b within the range of about 0 degrees to about −30 degrees from the transverse axis 106. The meeting location 100 may be positioned between the first axis 110 and the second axis 112.

Referring again to FIG. 2A, the flat portion 72 has a first end 120 and a second end 122. The first end 120 may be located at the coupling end 52 and the second end 122 may be located towards the intermediate portion 60 from the first end 120. In some embodiments, the second end 122 of the flat portion 72 is located a first distance 124 from the coupling end 52. The meeting location 100 may be within a second distance 126 from the coupling end 52. In general, the second distance 126 is less than the first distance 124. In some embodiments, the second distance 126 can be within a range of zero to 2 mm.

Figure 3A:
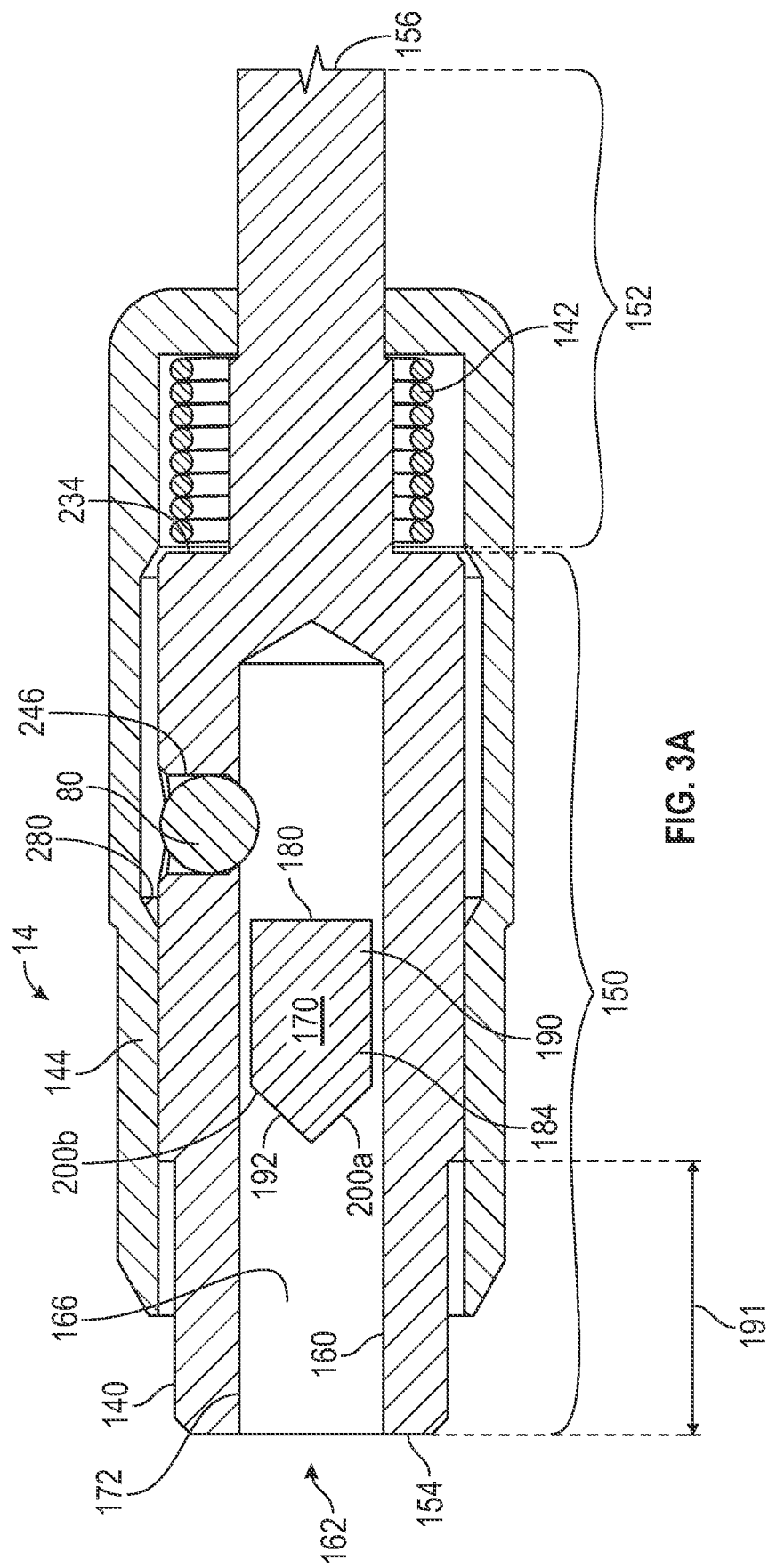
FIG. 3A is a cross-sectional side view of the quick connect interface of FIG. 1 showing, among other things, an alignment member within a bore of a socket portion of the quick connect interface, a ball bearing and a coupling sleeve in an unlocked position.
Figure 3B:
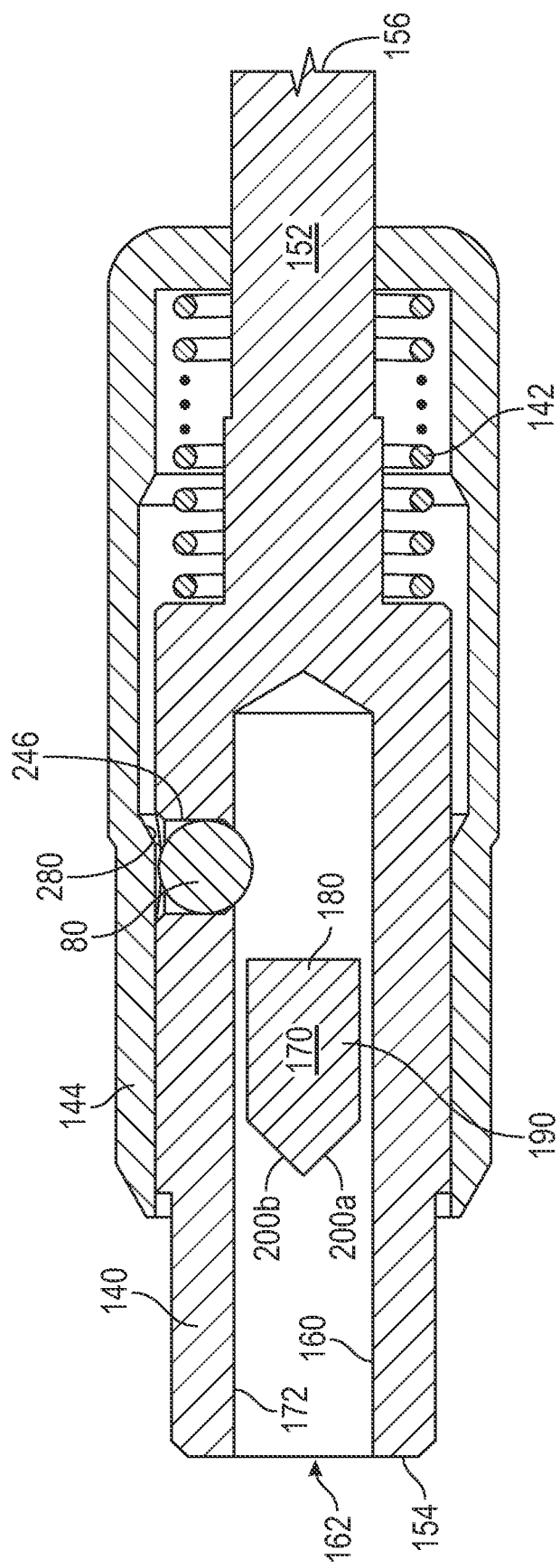
FIG. 3B is a cross-sectional side view of the quick connect interface of FIG. 1 showing, among other things, the alignment member within the bore of the socket portion of the quick connect interface, the ball bearing and the coupling sleeve in a locked position.

Referring now to FIGS. 3A and 3B, the quick connect interface 14 will be described. The quick connect interface 14 includes a body member 140, the bearing 80, a bias assembly 142, and a coupling sleeve 144. The sleeve 144 extends around at least a portion of the body member 140 and is slidably movable on the body member 140. In some embodiments, the coupling sleeve 144 surrounds the body member 140 in a concentric relationship. As will be described in more detail below, the body member 140, the bearing 80, the bias assembly 142, and the coupling sleeve 144 of the quick connect interface 14 are configured to receive and secure the coupling portion 58 of the replaceable tool 16 within the body member 140 of the quick connect interface 14. As previously mentioned, other than the components providing the self-centering function described in the present disclosure, the quick connect interface 14 may be constructed to conform to the requirements of an Association for Osteosynthesis (AO)-style quick connect interface, typically referred to simply as an "AO quick connect interface."

The body member 140 is provided with a socket portion 150 and shaft member 152. The body member 140 includes a first end 154 and a second end 156 opposite the first end 154. The longitudinal axis 18 extends through the body member 140 from the first end 154 to the second end 156. The socket portion 150 of the body member 140 extends from the first end 154 towards the second end 156. The shaft member 152 of the body member 140 extends from the socket portion 150 to the second end 156. The shaft member 152 is the portion of the quick connect interface 14 that may extend into the bore 40 of the drive mechanism 12 to secure the quick connect interface 14 to the handle portion 34 of the drive mechanism 12. It should also be understood that the bore 40 and the shaft member 152 may be shaped so that the bore 40 may receive the shaft member 152 without permitting rotation of the shaft member 152 relative to the handle portion 34.

Figure 5:
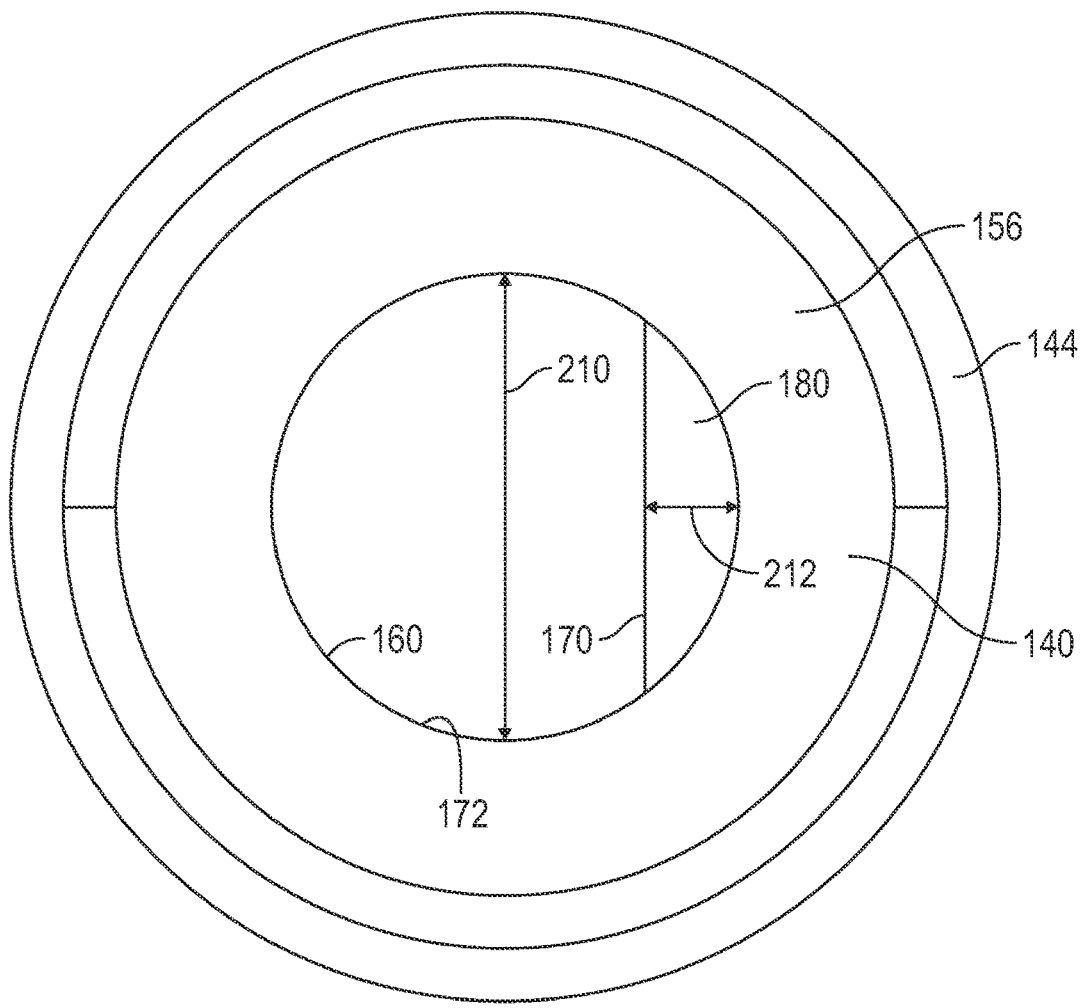
FIG. 5 is a front view of the quick connect interface showing relative dimensions of the bore within the socket portion and the alignment member.

The socket portion 150 includes an inner surface 160 defining an opening 162 at the first end 154, and defines a bore 166 extending from the opening 162 at the first end 154 towards the second end 156. The inner surface 160 is shaped to receive the coupling portion 58 of the replaceable tool 16. As best shown in FIG. 5, the inner surface 160 has a flat portion 170 and an arcuate portion 172 define a second D-shaped cross-section corresponding to the first D-shaped cross-section of the replaceable tool 16. The flat portion 170 and the arcuate portion 172 of the inner surface 160 may be sized to conform to requirements of the Association for Osteosynthesis (AO)-style quick connect interface.

The socket portion 150 of the body member 140 has an alignment member 180 within the bore 166. In some embodiments, the socket portion 150 of the body member 140 may be shaped to form the alignment member 180. In other embodiments, the alignment member 180 may be constructed separately and fixed to the inner surface 160 via welding, or one or more suitable fastener. The alignment member 180 has an outer surface 184 defining at least a portion of the flat portion 170 of the inner surface 160 of the socket portion 150. The alignment member 180 is positioned adjacent to and/or within the bore 166 a distance 191 from the first end 154. The alignment member 180 has a top surface 190 and a front surface 192 facing the first end 154 of the body member 140. The top surface 190 of the alignment member 180 defines at least a portion of the flat portion 170 of the inner surface 160. The front surface 192 has at least one alignment surface 200. In the example shown, the front surface 192 has a first alignment surface 200a and a second alignment surface 200b. The first alignment surface 200a extends at an angle 204 between about 30 degrees and about 60 degrees relative to the longitudinal axis 18. The second alignment surface 200b extends at an angle 206 between about 30 degrees and about 60 degrees relative to the longitudinal axis 18. In some embodiments, the first alignment surface 200a and the second alignment surface 200b form a V-shape.

As shown in FIG. 5, the bore 166 has a diameter 210 and the alignment member 180 has a height 212. The height 212 of the alignment member 180 is less than the diameter 210 of the bore 166 so as to allow for the arcuate portion 74 of the outer peripheral surface 70 of the shaft 50 to enter and exit the bore 166. In some embodiments, the height 212 of the alignment member 180 is in a range from 10% to 25% of the diameter 210 of the bore 166.

The first alignment surface 200a and the second alignment surface 200b of the alignment member 180 have a shape that upon interaction with one of the first bearing surface 90a and the second bearing surface 90b of the replaceable tool 16 causes the replaceable tool 16 to rotate about the longitudinal axis 18 thereby guiding the flat portion 72 (which may be referred to herein as a "first flat portion") of the replaceable tool 16 into alignment with the flat portion 170 (which may be referred to herein as a "second flat portion") of the alignment member 180.

Figure 4:
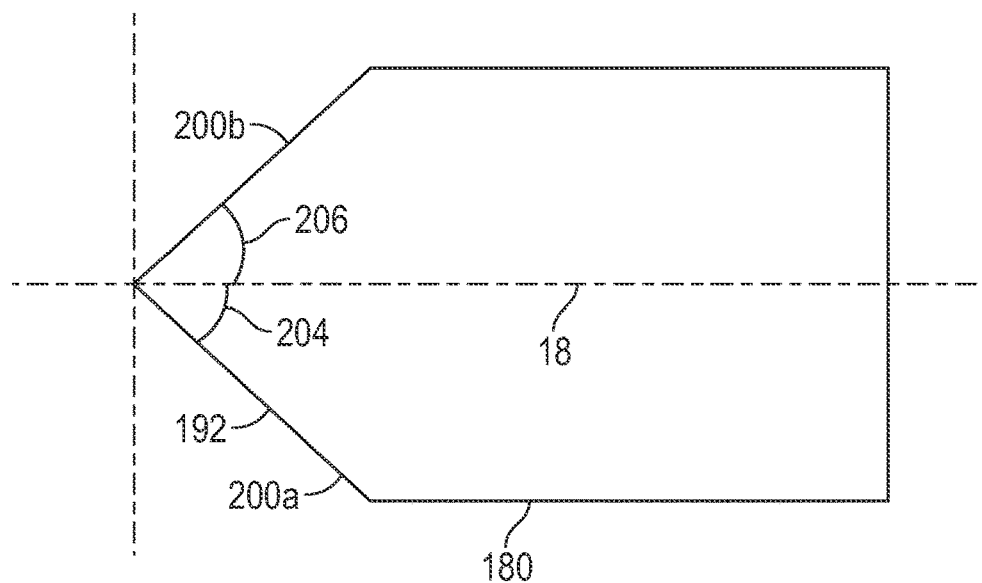
FIG. 4 is a top plan view of the alignment member constructed in accordance with the present disclosure.

As best shown in FIG. 4, the first alignment surface 200a and the second alignment surface 200b of the alignment member 180 may be planar and may be formed at non-normal angles relative to the longitudinal axis 18.

The bearing surface(s) 90 of the replaceable tool 16 and the alignment surface(s) 200a and 200b of the alignment member 180 are configured such that when the bearing surface(s) 90 are moved toward the alignment surface(s) 200a and 200b in a first direction 220 (see FIG. 1) at a first rate, the bearing surface(s) 90 and the alignment surface(s) 200a and 200b are engaged. Further linear motion of the bearing surface(s) 90 in the first direction 220 causes one of the bearing surfaces 90 to ride on one of the first alignment surface or the second alignment surface 200b converting the further linear motion of the bearing surface(s) 90 into a combination of (a) the further linear motion in the first direction 220 and (b) rotational motion. Thus, the bearing surface(s) 90 on the coupling portion 58 of the replaceable tool 16 and the alignment surfaces 200a and 200b of the alignment member 180 of the quick connect interface 14 are operable to translate linear motion into a combination of linear motion and rotational motion that serves to permit the user to insert the coupling portion 58 of the replaceable tool 16 into the bore 166 of the socket portion 150 of the quick connect interface 14 with a linear motion and automatically align the first D-shaped cross-section of the coupling portion 58 with the second D-shaped cross-section of the bore 166 of the socket portion 150 of the quick connect interface 14.

Figure 6A:
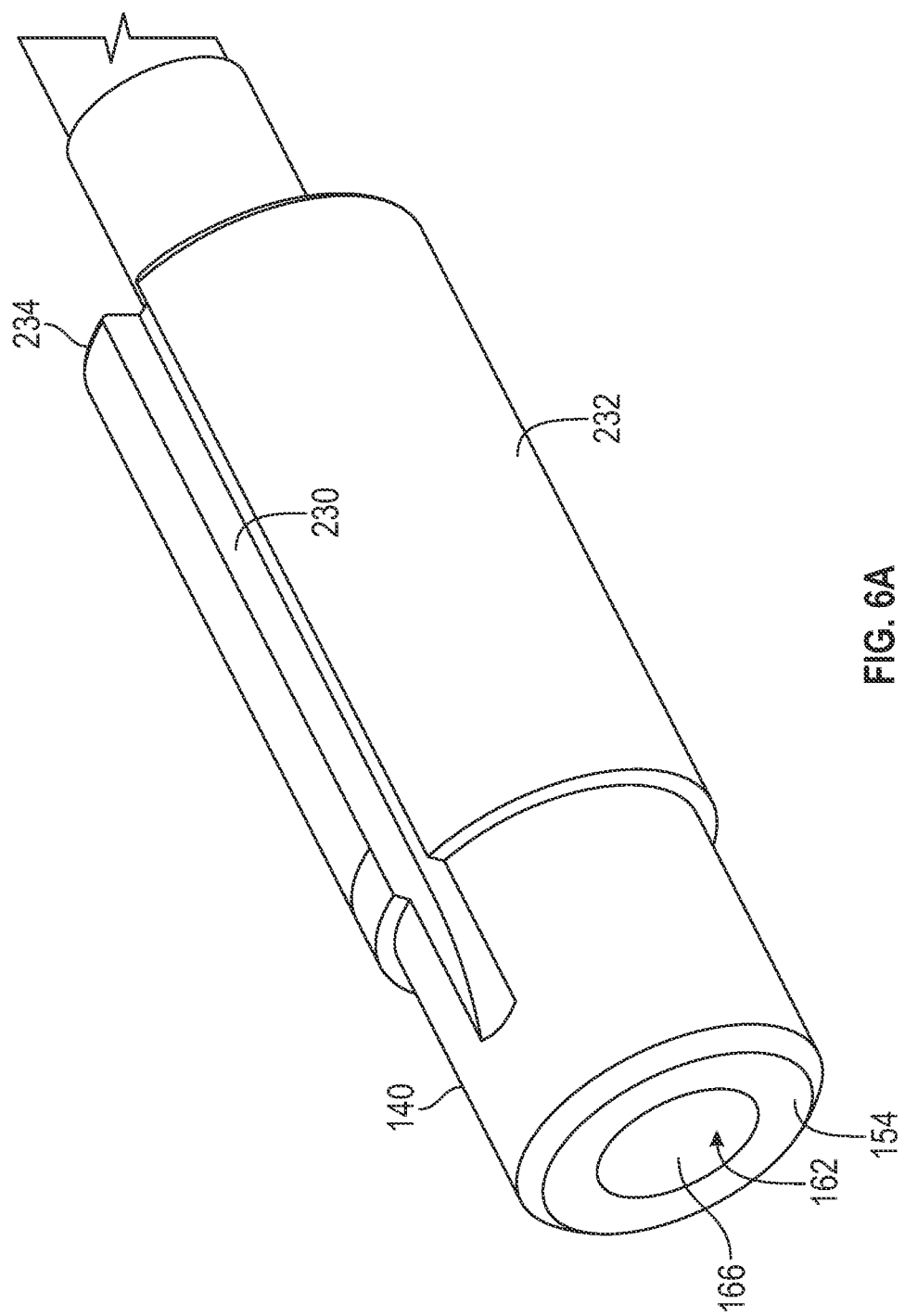
FIG. 6A is a perspective view of a body member of the quick connect interface showing, among other things, a linear groove and pin slot.
Figure 6B:
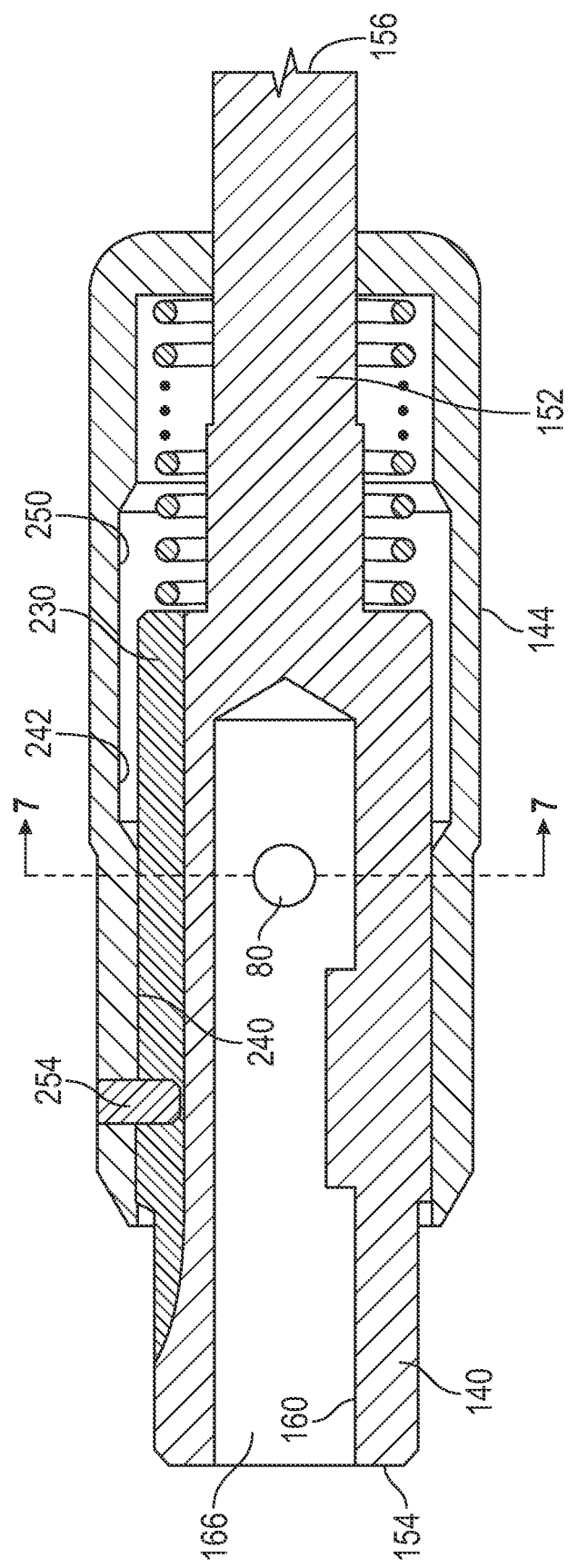
FIG. 6B is another cross-sectional side view of the quick connect interface of FIG. 1 showing, among other things, the linear groove and the pin slot.
Figure 7:
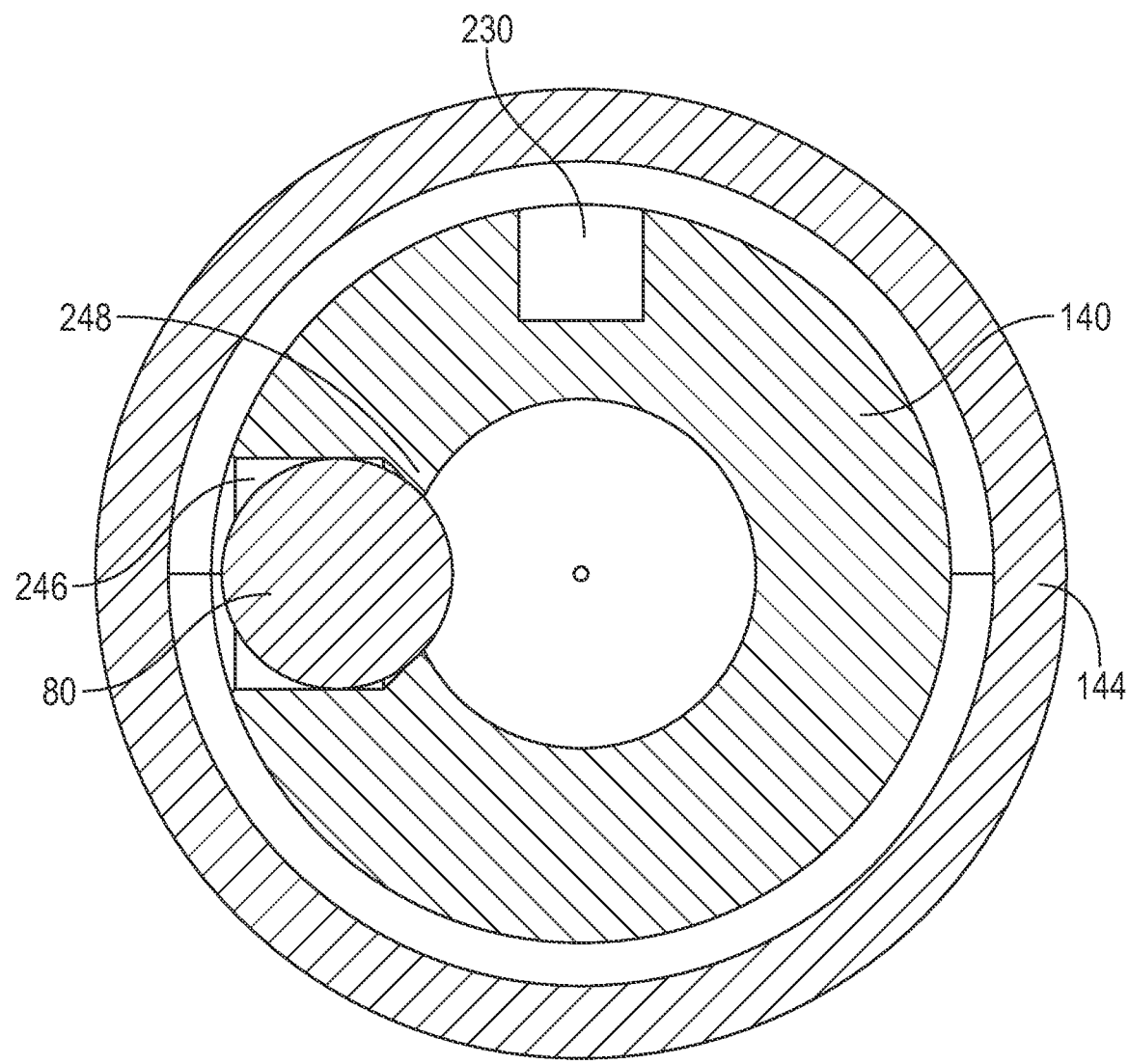
FIG. 7 is a cross-sectional front view of the quick connect interface of FIG. 1 showing, among other things, the sleeve in an unlocked position with an inner surface of the coupling sleeve spaced a distance away from the ball bearing.

Referring to FIGS. 6A and 6B, other components of the quick connect interface 14 will be described hereinafter. The socket portion 150 of the body member 140 may be provided with a linear groove 230 positioned in an outer surface 232 of the socket portion 141 extending from a rear end 234 of the socket portion 150 towards the first end 154.

The coupling sleeve 144 surrounds the socket portion 150 of the body member 140 and is slidably movable on the body member 140. The coupling sleeve 144 includes a first portion 240 and a second portion 242 with the first portion 240 positioned closer to the outer surface 232 than the second portion 242. The first portion 240 is shaped so as to urge the bearing 80 to partially extend through a hole 246 into the bore 166 of the socket portion 150. When the bearing 80 is maintained in a partially extended position through the hole 246 into the bore 166 of the socket portion 150, and the coupling portion 58 of the replaceable tool 16 is positioned within the bore 166, the bearing 80 extends into the peripheral groove 76 and functions to maintain the coupling portion 58 within the bore 166. The socket portion 150 includes a lip 248 extending around a circumference of the hole 246 at the inner surface 160. The bearing 80 has a diameter greater than the smallest diameter of the lip 248 at the inner surface 160 so that the bearing 80 may only partially cross the inner surface 160 of the socket portion 150. The second portion 242 is shaped so as to not urge the bearing 80 into the bore 166. When the second portion 242 overlaps the bearing 80, the bearing 80 may freely move outside of the bore 166 when force is applied to the bearing 80. Thus, when the coupling sleeve 144 is moved such that the second portion 242 overlaps the bearing 80, the coupling portion 58 of the replaceable tool 16 can be moved into the bore 166 and/or removed from the bore 166 without substantial interference from the bearing 80.

In some embodiments, the coupling sleeve 144 includes an inner surface 250 positioned adjacent to the outer surface 232 of the socket portion 150 of the body member 140. To guide the coupling sleeve 144 on the outer surface 232 of the socket portion 150, the coupling sleeve 144 may include a pin member 254 connected to the coupling sleeve 144 and extending from the inner surface 250 and into the linear groove 230. The linear groove 230 guides the pin member 254 in a linear direction as the coupling sleeve 144 is moved between a locked position in which the first portion 240 overlaps the bearing 80 and an unlocked position in which the second portion 242 overlaps the bearing 80.

The dimensions of the linear groove 230 may be compatible with the pin member 254. The engagement of the pin member 254 within the linear groove 230 removes a rotational degree of freedom of the coupling sleeve 144 with respect to the body member 140. The engagement of the pin member 254 within the linear groove 230 enables the coupling sleeve 144 to slide along the longitudinally axis 18 from the locked position to the unlocked position, provided a force is applied by the user to the coupling sleeve 144 toward the first end 154 that is sufficient to overcome the force of the bias assembly 142. When the force applied by the user is removed from the coupling sleeve 144, the bias assembly 142 applies a force to the coupling sleeve 144 to move the coupling sleeve toward the second end 156 thereby restoring the coupling sleeve 144 to the locked position.

As previously mentioned, the quick connect interface 14 is provided with the bearing 80. The peripheral groove 76 in some embodiments is configured to receive at least a portion of the bearing 80 to maintain the coupling portion 58 of the replaceable tool 16 within the bore of the quick connect interface 14. The bearing 80 is housed within the hole 246. The hole 246 may be positioned so that the bearing 80 is in substantial alignment with the peripheral groove 76 in the coupling portion 58.

The bias assembly 142, as shown in FIG. 3A, may surround a portion of the shaft member 152, and may urge the coupling sleeve 144 toward the second end 156 of the body member 140, so that, when at steady state, the coupling sleeve 144 is in the locked position. In one embodiment the bias assembly 142 is a compression spring that engages with the rear end 234 of the socket portion 150 of the body member 140 and the inner surface 250 of the coupling sleeve 144. In use, a user may pull the coupling sleeve 144 toward the first end 154, to the unlocked position, against the resistance of the bias assembly 142.

The coupling sleeve 144 may surround portions of the socket portion 150 and the shaft member 152, the bearing 80, and other components of the quick connect interface 14. The coupling sleeve 144 may slide from the unlocked position, where the coupling sleeve 144 is shifted towards the first end 154 of the socket portion 150, to a locked position, where the coupling sleeve 144 is shifted towards the second end 156 of the body member 140.

The coupling sleeve 144 slides from an unlocked position (FIG. 3A), where the sleeve 144 is shifted towards the first end 154 of the body member 140 of the quick connect interface 14, to a locked position (FIG. 3B), where the coupling sleeve 144 is shifted towards the second end 156 of the body member 140. The bias assembly 142, e.g., a compression spring, may surround the shaft member 152, and may urge the coupling sleeve 144 towards the second end 156, so that, when at rest, the coupling sleeve 144 is in the locked position. Referring to FIGS. 3A and 3B-4, the coupling sleeve 144 may also include a camming ramp 280 formed in the interior surface 250 of the coupling sleeve 144, proximate to the bearing 80. The camming ramp 280 functions to urge the bearing 80 into the hole 246 as the coupling sleeve 144 is slid from the unlocked position (FIG. 3A) to the locked position (FIG. 3B).

When the coupling sleeve 144 is returned to the unlocked position (FIG. 3A), pressure on the bearing 80 from the camming ramp 280 may be removed. The bearing 80 is allowed to recess in the hole 246 from the bore 166. The coupling portion 58 of the replaceable tool 16 may then be removed from the quick connect interface 14.

To use the coupling assembly 13, the coupling portion 58 (having a first D-shaped cross-section) is inserted into the bore 166 (having a second D-shaped cross-section) within the socket portion 150 of the body member 140 of the quick connect interface 14 until the bearing surface 90*a* or 90*b* having a shape conforming to a partial spiral around the longitudinal axis 18 of the replaceable tool 16 engages the alignment member 180 within the bore 166 causing rotation of the coupling end 52 of the replaceable tool 16 to align the flat portion 72 with the flat portion 170. In some embodiments, the method further comprises moving the coupling sleeve 144 surrounding at least a portion of the body member 140 to an unlocked position prior to inserting the coupling portion 58 into the bore 166 and maintaining the coupling sleeve 144 in the unlocked position during the step of inserting the coupling portion 58 into the bore 166. Once the coupling portion 58 is full inserted into the bore 166, the coupling sleeve 144 is moved to the locked position to maintain a portion of the bearing 80 in the peripheral groove 76 thereby preventing removal of the coupling portion 58 from the bore 166.

To make the replaceable tool 16, at least one bearing surface 90*a* and/or 90*b* having a partial spiral shape is formed on the coupling portion 58. The coupling portion 58 has a D-shaped cross-section of the shaft 50 of the replaceable tool 16. The shaft 50 having the tool end 54 opposite to the coupling end 52, and the longitudinal axis 18 extending from the tool end 54 to the coupling end 52. The coupling portion 58 extending from the coupling end 52 towards the tool end 54.

In some embodiments, the bearing surface 90 is a first bearing surface 90*a*, and wherein the step of forming the first bearing surface 90*a* is defined further as forming the bearing surface such that the partial spiral extends around the longitudinal axis 18 in a clockwise direction.

In some embodiments, the second bearing surface 90*b* having a second shape conforming to a second partial spiral extending around the longitudinal axis 18 is formed and located at the coupling end 52 of the shaft 50. The second bearing surface 90*b* extends in a counter-clockwise direction.

It is discussed above that the quick connect interface 14 may be an AO quick connect interface. It should be understood that the techniques described herein may be readily adapted to work with pull or push variants of this type of interface. It should also be understood that at least some of the techniques may be readily adapted to work with other types of interfaces, for example, ¼ square, Zimmer, Hudson or other types of interfaces in which the coupling portion 58 of the shaft 50 does not include a D-shaped cross-section. It should also be understood that the various components of the quick connect interface 14 can be made utilizing various manufacturing techniques, such as 3D printing, milling, molding or the like, and then assembled. In some embodiments, the entire quick connect interface 14 can be made in an assembled form using a 3D printer and 3D printing techniques.

Similarly, while it is discussed above that one bearing 80 is used, it should be understood that a different number of bearings 80 can be used, such as only one, or two or more. Further, the bearing 80 need not be a ball bearing. For example, a cylindrical roller bearing may be substituted for the bearing 80 discussed above.

Further, while it is discussed above that the bias assembly 142 include a compression spring, it should be understood that other types of springs may be used for urging the coupling sleeve 144 to a locked position. For example, in some embodiments, one or more tension springs may be employed.

It should be understood that the quick connect interface 14 and the replaceable tool 16 may be constructed from a variety of materials, including stainless steel, titanium, aluminum, other metals, plastics, and combinations thereof.

The foregoing description provides illustration and description, but is not intended to be exhaustive or to limit the inventive concepts to the precise form disclosed. Modifications and variations are possible in light of the above teachings or may be acquired from practice of the methodologies set forth in the present disclosure.

Even though particular combinations of features are recited in the claims and/or disclosed in the specification, these combinations are not intended to limit the disclosure. In fact, many of these features may be combined in ways not specifically recited in the claims and/or disclosed in the specification. Although each dependent claim listed below may directly depend on only one other claim, the disclosure includes each dependent claim in combination with every other claim in the claim set.

No element, act, or instruction used in the present application should be construed as critical or essential to the invention unless explicitly described as such outside of the preferred embodiment. Further, the phrase "based on" is intended to mean "based, at least in part, on" unless explicitly stated otherwise.

What is claimed is:

1. A replaceable tool, comprising:
   a shaft having a tool end, a coupling end opposite the tool end, and a longitudinal axis extending between the coupling end and the tool end, the shaft having:
      a tool portion defining the tool end;
      a coupling portion defining the coupling end, the coupling portion having an outer peripheral surface shaped into a flat portion coextensive with an arcuate portion cooperatively forming a D-shaped cross-section, the flat portion and the arcuate portion extending along at least a portion of the longitudinal axis;
      the outer peripheral surface defining a peripheral groove extending transversely with respect to the longitudinal axis;
      the peripheral groove configured to receive at least a portion of a bearing; and
      the outer peripheral surface also defining a bearing surface having a shape conforming to a partial spiral extending around the longitudinal axis and located at the coupling end of the shaft.

2. The replaceable tool of claim 1, wherein the bearing surface has a first end and a second end opposed from the first end, the first end originating at the coupling end of the shaft and the second end terminating at the flat portion of the outer peripheral surface of the shaft.

3. The replaceable tool of claim 2, wherein the bearing surface extends at an angle between about 30 degrees and about 150 degrees relative to the longitudinal axis of the replaceable tool.

4. The replaceable tool of claim 1, wherein the bearing surface is a first bearing surface, wherein the shape is a first shape, and wherein the partial spiral is a first partial spiral, and further comprising a second bearing surface having a second shape conforming to a second partial spiral extending around the longitudinal axis and located at the coupling end of the shaft, the first bearing surface extending in a clockwise direction around the longitudinal axis, and the second bearing surface extending in a counter-clockwise direction around the longitudinal axis.

5. The replaceable tool of claim 4, wherein the coupling portion has a length, and wherein the first bearing surface and the second bearing surface meet within a distance of 0% to 10% of the length from the coupling end of the shaft.

6. The replaceable tool of claim 5, wherein the first bearing surface and the second bearing surface meet at a meeting location, the meeting location being within a range of plus 150 degrees from the flat portion to minus 150 degrees from the flat portion.

7. The replaceable tool of claim 5, wherein the flat portion has an end located a first distance from the coupling end, and wherein the first bearing surface and the second bearing surface meet within a second distance from the coupling end, the second distance being less than the first distance.

8. A quick connect interface, comprising:
   a body member having a socket portion and a shaft member, the body member including a first end and a second end opposite the first end, and a longitudinal axis extending through the body member from the first end to the second end, the shaft member extending from the socket portion;
   the socket portion having an outer surface and an inner surface, the socket portion having a front end and a rear end, the inner surface defining an opening at the front end, and defining a bore extending from the opening at the front end towards the rear end, the inner surface having a flat portion and an arcuate portion coextensive with the flat portion cooperatively forming a D-shaped cross-section;
   the socket portion having an alignment member within the bore, the alignment member having an outer surface defining at least a portion of the flat portion of the inner surface of the socket portion;
   the alignment member having a front surface facing the front end of the socket portion; and
   the front surface having at least one alignment surface extending at an angle between 30 degrees and 60 degrees relative to the longitudinal axis;
   the socket portion having a hole extending from the outer surface to the inner surface;
   a ball bearing positioned in the hole in the socket portion;
   a coupling sleeve extending around at least a portion of the socket portion, the coupling sleeve including a first portion and a second portion, the first portion being shaped so as to urge the ball bearing to partially extend through the hole into the bore of the socket portion, the second portion being shaped so as to not urge the ball bearing; and
   a bias assembly positioned adjacent to the socket portion and the coupling sleeve and operable to urge the coupling sleeve away from the rear end of the socket portion to a locked position.

9. The quick connect interface of claim 8, wherein the hole has a lip extending around a circumference of the hole at the inner surface, the ball bearing having a diameter greater than a smallest diameter of the lip at the inner surface so that the ball bearing may only partially cross a plane of the inner surface of the socket portion.

10. The quick connect interface of claim 9, wherein the sleeve is movable along the socket portion from an unlocked position to the locked position.

11. The quick connect interface of claim 9, wherein the socket portion has a linear groove in the outer surface defining an opening at the rear end and extending from the opening at the rear end towards the front end.

12. The quick connect interface of claim 11, wherein the coupling sleeve has a pin extending from an inner surface of the coupling sleeve into the linear groove.

13. The quick connect interface of claim 9, wherein the bore has a diameter, and wherein the alignment member has a height in a range from 10% to 25% of the diameter of the bore.

14. The quick connect interface of claim 9, wherein the at least one alignment surface is planar.

15. The quick connect interface of claim 8, wherein the at least one alignment surface is a first alignment surface, and wherein the front surface of the alignment member further comprises a second alignment surface extending away from the first alignment surface, the first alignment surface and the second alignment surface forming a V-shape.

16. The quick connect interface of claim 15, wherein the second alignment surface extends at an angle between 30 degrees and 60 degrees relative to the longitudinal axis.

17. The quick connect interface of claim 15, wherein the first alignment surface and the second alignment surface are arranged to form an angle in a range from 60 degrees to 90 degrees.

18. A method, comprising:
inserting a coupling portion having a first D-shaped cross-section of a replaceable tool into a bore having a second D-shaped cross-section within a socket portion of a body member of a quick connect interface until a bearing surface having a shape conforming to a partial spiral around a longitudinal axis of the replaceable tool engages an alignment member within the bore causing rotation of the coupling end of the replaceable tool.

19. The method of claim 18, further comprising moving a coupling sleeve surrounding at least a portion of the body member to an unlocked position prior to inserting the coupling portion into the bore and maintaining the coupling sleeve in the unlocked position during the step of inserting the coupling portion into the bore.

20. The method of claim 19, further comprising moving the coupling sleeve to a locked position after the coupling portion is inserted into the bore.

21. A method of making a replaceable tool, comprising:
forming a bearing surface having a partial spiral shape on a coupling portion having a D-shaped cross-section of a shaft of the replaceable tool, the shaft having a tool end opposite to a coupling end, and a longitudinal axis extending from the tool end to the coupling end, the coupling portion extending from the coupling end towards the tool end.

22. The method of claim 21, wherein the bearing surface is a first bearing surface, and wherein the step of forming the first bearing surface is defined further as forming the bearing surface such that the partial spiral extends around the longitudinal axis in a clockwise direction.

23. The method of claim 22, further comprising forming a second bearing surface having a second shape conforming to a second partial spiral extending around the longitudinal axis and located at the coupling end of the shaft, the second bearing surface extending in a counter-clockwise direction.

* * * * *